United States Patent
Hole et al.

(10) Patent No.: US 7,531,133 B2
(45) Date of Patent: May 12, 2009

(54) USE OF NITRIC OXIDE GAS IN AN EXTRACORPOREAL CIRCUITRY TO TREAT BLOOD PLASMA

(75) Inventors: Douglas Hole, Edmonton (CA); Christopher C. Miller, North Vancouver (CA)

(73) Assignee: Pulmonox Technologies Corporation, Edmonton, Alberta (CA)

( * ) Notice: Subject to any disclaimer, the term of this patent is extended or adjusted under 35 U.S.C. 154(b) by 327 days.

(21) Appl. No.: 11/445,965

(22) Filed: Jun. 1, 2006

(65) Prior Publication Data

US 2007/0014688 A1    Jan. 18, 2007

Related U.S. Application Data

(63) Continuation-in-part of application No. 10/658,665, filed on Sep. 9, 2003.

(60) Provisional application No. 60/409,400, filed on Sep. 10, 2002.

(51) Int. Cl.
*A61M 1/00* (2006.01)
*A61M 37/00* (2006.01)
*C02F 1/44* (2006.01)

(52) U.S. Cl. .............. 422/44; 422/48; 604/4.01; 604/5.01; 604/5.04; 604/23; 210/645

(58) Field of Classification Search ............. 604/4.01, 604/5.01, 5.02, 5.04, 6.09, 6.11, 6.13, 6.14, 604/6.08, 23, 25; 424/140.1, 158.1, 134.1; 422/44–46, 48; 210/645
See application file for complete search history.

(56) References Cited

U.S. PATENT DOCUMENTS

| | | |
|---|---|---|
| 3,036,584 A | 5/1962 | Lee |
| 3,192,106 A | 6/1965 | Bracken et al. |
| 4,127,121 A | 11/1978 | Westenskow et al. |
| 4,191,952 A | 3/1980 | Schreiber et al. |
| 4,224,941 A | 9/1980 | Stivala |
| 4,328,823 A | 5/1982 | Schreiber |
| 4,336,798 A | 6/1982 | Beran |
| 4,345,612 A | 8/1982 | Koni et al. |
| 4,442,856 A | 4/1984 | Betz et al. |
| 4,608,041 A | 8/1986 | Nielsen |

(Continued)

FOREIGN PATENT DOCUMENTS

| | | |
|---|---|---|
| DE | 003713396 A1 | 11/1998 |
| EP | 0640356 A1 | 3/1995 |
| EP | 0640357 A1 | 3/1995 |
| EP | 0659445 A1 | 6/1995 |
| EP | 0659445 B1 | 6/1995 |

(Continued)

OTHER PUBLICATIONS

Croen, KD, Evidence for an antiviral effect of Nitric Oxide. J Clin Invest 91:2446-2452, 1993.*

(Continued)

*Primary Examiner*—Leslie R Deak
(74) *Attorney, Agent, or Firm*—Sidley Austin LLP

(57) ABSTRACT

A method of reducing pathogens in blood by exposure to a nitric oxide containing gas in an extracorporeal circuitry is provided. The method includes: obtaining blood from a mammal or a blood source, separating the blood into plasma and blood cells, exposing the plasma to nitric oxide containing gas, combining the exposed plasma with the blood cells, reducing nitric oxide content in the recombined blood, and returning the blood to the mammal or blood source.

42 Claims, 3 Drawing Sheets

U.S. PATENT DOCUMENTS

| | | | |
|---|---|---|---|
| 4,611,590 A | 9/1986 | Ryschka et al. |
| 4,614,513 A * | 9/1986 | Bensinger .................. 604/5.01 |
| 4,770,168 A | 9/1988 | Rusz et al. |
| 4,905,685 A | 3/1990 | Olsson et al. |
| 4,954,526 A | 9/1990 | Keefer |
| 5,154,697 A | 10/1992 | Loori |
| 5,155,137 A | 10/1992 | Keefer et al. |
| 5,159,924 A | 11/1992 | Cegielski et al. |
| 5,197,462 A | 3/1993 | Falb et al. |
| 5,396,882 A | 3/1995 | Zapol |
| 5,423,313 A | 6/1995 | Olsson et al. |
| 5,427,797 A | 6/1995 | Frostell et al. |
| 5,485,827 A | 1/1996 | Zapol et al. |
| 5,514,204 A | 5/1996 | Sheu et al. |
| 5,519,020 A | 5/1996 | Smith et al. |
| 5,531,218 A | 7/1996 | Krebs |
| 5,536,241 A | 7/1996 | Zapol |
| 5,558,083 A | 9/1996 | Bathe et al. |
| 5,570,683 A | 11/1996 | Zapol |
| 5,615,669 A | 4/1997 | Olsson et al. |
| 5,632,981 A | 5/1997 | Saavedra et al. |
| 5,648,101 A | 7/1997 | Tawashi |
| 5,650,442 A | 7/1997 | Mitchell et al. |
| 5,651,358 A | 7/1997 | Briend et al. |
| 5,676,963 A | 10/1997 | Keefer et al. |
| 5,688,236 A | 11/1997 | Gragg |
| 5,692,497 A | 12/1997 | Schnitzer et al. |
| 5,700,830 A | 12/1997 | Korthuis et al. |
| 5,713,349 A | 2/1998 | Keaney |
| 5,722,392 A | 3/1998 | Skimming et al. |
| 5,725,492 A * | 3/1998 | Igo et al. .................. 604/6.11 |
| 5,732,693 A | 3/1998 | Bathe et al. |
| 5,765,548 A | 6/1998 | Perry |
| 5,789,447 A | 8/1998 | Wink, Jr. et al. |
| 5,810,795 A | 9/1998 | Westwood |
| 5,814,666 A | 9/1998 | Green et al. |
| 5,814,667 A | 9/1998 | Mitchell et al. |
| 5,823,180 A | 10/1998 | Zapol |
| 5,834,030 A | 11/1998 | Bolton |
| 5,837,736 A | 11/1998 | Mitchell et al. |
| 5,839,433 A | 11/1998 | Higgenbottam |
| 5,840,759 A | 11/1998 | Mitchell et al. |
| 5,845,633 A | 12/1998 | Psaros |
| 5,873,359 A | 2/1999 | Zapol et al. |
| 5,885,621 A | 3/1999 | Head et al. |
| 5,904,938 A | 5/1999 | Zapol et al. |
| 5,918,596 A | 7/1999 | Heinonen |
| 5,957,880 A | 9/1999 | Igo et al. |
| 6,000,403 A | 12/1999 | Cantwell |
| 6,060,020 A | 5/2000 | Piuk et al. |
| 6,063,407 A | 5/2000 | Zapol et al. |
| 6,067,983 A | 5/2000 | Stenzler |
| 6,071,254 A | 6/2000 | Augustine |
| 6,073,627 A | 6/2000 | Sunnen |
| 6,083,209 A | 7/2000 | Marasco, Jr. |
| 6,089,229 A | 7/2000 | Bathe et al. |
| 6,103,275 A | 8/2000 | Seitz et al. |
| 6,109,260 A | 8/2000 | Bathe |
| 6,110,895 A | 8/2000 | Rodgers et al. |
| 6,125,846 A | 10/2000 | Bathe et al. |
| 6,131,572 A | 10/2000 | Heinonen |
| 6,142,147 A | 11/2000 | Head et al. |
| 6,158,434 A | 12/2000 | Lugtigheid et al. |
| 6,160,021 A | 12/2000 | Lerner et al. |
| 6,164,276 A | 12/2000 | Bathe et al. |
| 6,190,704 B1 | 2/2001 | Murrell |
| 6,200,558 B1 | 3/2001 | Saavedra et al. |
| 6,232,336 B1 | 5/2001 | Hrabie et al. |
| 6,265,420 B1 * | 7/2001 | Lai .......................... 514/310 |
| 6,270,779 B1 | 8/2001 | Fitzhugh et al. |
| 6,358,536 B1 | 3/2002 | Thomas |
| 6,379,660 B1 | 4/2002 | Saavedra et al. |
| 6,432,077 B1 | 8/2002 | Stenzler |
| 6,472,390 B1 | 10/2002 | Stamler et al. |
| 6,494,314 B1 | 12/2002 | Lamborne et al. |
| 6,511,991 B2 | 1/2003 | Hrabie et al. |
| 6,555,058 B2 | 4/2003 | Kamibayashi et al. |
| 6,571,790 B1 | 6/2003 | Weinstein |
| 6,581,599 B1 | 6/2003 | Stenzler |
| 6,601,580 B1 | 8/2003 | Bloch et al. |
| 6,673,338 B1 | 1/2004 | Arnold et al. |
| 6,703,046 B2 | 3/2004 | Fitzhugh et al. |
| 6,706,274 B2 | 3/2004 | Herrmann et al. |
| 6,715,485 B1 | 4/2004 | Djupesland |
| 6,747,062 B2 | 6/2004 | Murrell |
| 6,750,254 B2 | 6/2004 | Hrabie et al. |
| 6,758,214 B2 | 7/2004 | Fine et al. |
| 6,780,849 B2 | 8/2004 | Herrmann et al. |
| 6,786,217 B2 | 9/2004 | Stenzler |
| 6,793,644 B2 | 9/2004 | Stenzler |
| 6,796,966 B2 | 9/2004 | Thomas |
| 6,811,965 B2 | 11/2004 | Vodovotz et al. |
| 6,867,194 B2 | 3/2005 | Wang et al. |
| 6,887,485 B2 | 5/2005 | Fitzhugh et al. |
| 6,911,478 B2 | 6/2005 | Hrabie et al. |
| 6,920,876 B2 | 7/2005 | Miller et al. |
| 6,938,357 B2 | 9/2005 | Hauch |
| 6,949,530 B2 | 9/2005 | Hrabie et al. |
| 7,048,951 B1 | 5/2006 | Seitz et al. |
| 7,105,502 B2 | 9/2006 | Arnold et al. |
| 7,118,767 B2 | 10/2006 | Kim et al. |
| 7,122,018 B2 | 10/2006 | Stenzler et al. |
| 7,199,154 B2 | 4/2007 | Berthelette et al. |
| 2002/0069877 A1 | 6/2002 | Villareal |
| 2002/0082566 A1 | 6/2002 | Stenzler |
| 2002/0119115 A1 | 8/2002 | Keefer et al. |
| 2002/0138051 A1 | 9/2002 | Hole et al. |
| 2002/0155164 A1 | 10/2002 | Figley et al. |
| 2002/0156416 A1 | 10/2002 | Stenzler |
| 2002/0169202 A1 | 11/2002 | Kazutami et al. |
| 2003/0039697 A1 | 2/2003 | Zhao et al. |
| 2003/0150457 A1 | 8/2003 | Miller et al. |
| 2003/0165578 A1 | 9/2003 | Murrell |
| 2003/0203915 A1 | 10/2003 | Fang et al. |
| 2003/0215528 A1 | 11/2003 | Graham et al. |
| 2003/0228564 A1 | 12/2003 | Edirch et al. |
| 2004/0009238 A1 | 1/2004 | Miller et al. |
| 2004/0043026 A1 | 3/2004 | Tuan et al. |
| 2004/0081580 A1 | 4/2004 | Hole et al. |
| 2004/0112378 A1 | 6/2004 | Djupesland |
| 2004/0131703 A1 | 7/2004 | Bach et al. |
| 2004/0163647 A1 | 8/2004 | Figley et al. |
| 2004/0180863 A1 | 9/2004 | Hrabie et al. |
| 2004/0259840 A1 | 12/2004 | Hermann et al. |
| 2005/0016427 A1 | 1/2005 | Memory |
| 2005/0079148 A1 | 4/2005 | Fitzhugh et al. |
| 2005/0137521 A1 | 6/2005 | Stenzler |
| 2005/0142217 A1 | 6/2005 | Adams et al. |
| 2005/0148566 A1 | 7/2005 | Waterhouse et al. |
| 2005/0171066 A1 | 8/2005 | Shami |
| 2005/0191372 A1 | 9/2005 | Stenzler et la. |
| 2005/0217668 A1 | 10/2005 | Figley et al. |
| 2005/0217679 A1 | 10/2005 | Miller et al. |
| 2005/0251117 A1 | 11/2005 | Anderson et al. |
| 2005/0265958 A1 | 12/2005 | West et al. |
| 2005/0288260 A1 | 12/2005 | Hrabie et al. |
| 2006/0008529 A1 | 1/2006 | Meyerhoff et al. |
| 2006/0068031 A1 | 3/2006 | Miller et al. |
| 2006/0147553 A1 | 7/2006 | Miller et al. |
| 2007/0065473 A1 | 3/2007 | Miller et al. |
| 2007/0086954 A1 | 4/2007 | Miller et al. |
| 2007/0088316 A1 | 4/2007 | Stenzler et al. |

| | | |
|---|---|---|
| 2007/0104653 A1 | 5/2007 | Miller et al. |

FOREIGN PATENT DOCUMENTS

| | | |
|---|---|---|
| EP | 1243278 A2 | 9/2002 |
| FR | 2656218 | 6/1991 |
| JP | 3-139364 | 6/1991 |
| JP | 3-207365 | 9/1991 |
| KR | 202066 | 6/1999 |
| WO | WO 92/17445 | 10/1992 |
| WO | WO 93/15779 | 8/1993 |
| WO | WO 93/17741 | 9/1993 |
| WO | WO 95/09612 | 4/1995 |
| WO | WO 96/00006 | 1/1996 |
| WO | WO 96/22803 | 8/1996 |
| WO | WO 96/25184 | 8/1996 |
| WO | WO 96/31217 | 10/1996 |
| WO | WO 98/01142 | 1/1998 |
| WO | WO 99/49921 | 10/1999 |
| WO | WO 00/07653 | 2/2000 |
| WO | WO 00/30659 | 6/2000 |
| WO | WO 01/65935 A1 | 9/2001 |
| WO | WO 02/056864 A2 | 7/2002 |
| WO | WO 03/066109 A1 | 8/2003 |
| WO | WO 2005/060603 A3 | 11/2005 |
| WO | WO 2005/110052 A3 | 11/2005 |
| WO | WO 2005/110441 A2 | 11/2005 |

OTHER PUBLICATIONS

Ray, James D. et al., "A New Method of Preparing Nitric Oxide," Contribution from the Department of Chemistry, Stanford University (1956).

Shank, J. L. et al., "The Effect of Nitric Oxide on Bacteria," Applied Microbio, No. 10, 189-189 (1962).

Norman, C. et al., "Nitrogen Oxides in Tobacco Smoke," Nature, vol. 205, No. 4971, pp. 915-916, (Feb. 1965).

Canetti, G., "Present aspects of bacterial resistance in tuberculosis," Am. Rev. Respir. Dis. 92:687-703 (1965).

Bass, H. et al., "Regional structure and function in brochiectasis," Am. Rev. Respir. Dis. 97:598-609 (1968).

Contractor, A. M. et al., "Development and Evaluation of an Inhalation Aerosol of Nitroglycerin," Journal of Pharmaceutical Sciences, vol. 63, No. 6, pp. 907-911 (Jun. 1974).

Oda, H. et al., "Nitrosyl-Hemoglobin Formation in the Blood of Animals Exposed to Nitric Oxide," Archives of Environmental Health, vol. 30, No. 7, pp. 453-456 (Sep. 1975).

Katsuki, S. et al., "Stimulation of Guanylate Cyclase by Sodium Nitroprusside, Nitroglycerin and Nitric Oxide in Various Tissue Preparations and Comparison to the Effects of Sodium Azide and Hydroxylamine," Journal of Cyclic Nucleotide Research, vol. 3, pp. 23-25 (1977).

Hugod, C., "Effect of exposure of 43 PPM nitric oxide and 3.6 PPM nitrogen dioxide on rabbit lung," Arch. Occup. Environ. Health 42:159-167 (1979).

Yoshida, J. et al., "Metabolic Fate of Nitric Oxide," Int Arch Occup Environ Health, vol. 46, No. 1, pp. 71-77 (Apr. 1980).

Borland, C., "The Fate of Inhaled Nitric Oxide," Clinical Science, Abstract No. 104, p. 37P (1983).

Mancinelli et al., "Effects of Nitric Oxide and Nitrogen Dioxide on Bacterial Growth," Applied and Environmental Microbiology, vol. 46, No. 1, pp. 198-202 (Jul. 1983).

Demling, R. H. et al., "The Pulmonary and Systemic Response to Recurrent Endotoxemia in the Adult Sheep," Surgery, vol. 100, No. 5, pp. 876-883 (Nov. 1986).

Higenbottam, T., "Primary Pulmonary Hypertension," British Medical Journal, vol. 293, pp. 1456-1457 (Dec. 1986).

Higenbottam, T. et al., "Primary Pulmonary Hypertension," British Medical Journal, vol. 294, p. 705 (Mar. 1987).

Palmer, R.M.J. et al., "Nitric Oxide Release Accounts for the Biological Activity of Endothelium-Derived Relaxing Factor," Nature, vol. 327, pp. 524-526 (Jun. 1987).

Ignarro, L. J. et al., "Endothelium-Derived Relaxing Factor Produced and Released From Artery and Vein is Nitric Oxide," Proceedings of the National Academy of Sciences of the United States of America, vol. 84, No. 24, pp. 9265-9269 (Dec. 1987).

Higenbottam, T. W. et al., "Inhaled 'Endothelium Derived-Relaxing Factor' (EDRF) in Primary Hypertension (PPH)," Abstract, American Review of Respiratory Disease, Suppl., vol. 137, No. 4, Part 2, p. 107 (Apr. 1988).

Ignarro, L. J. et al., "Endothelium-Derived Relaxing Factor and Nitric Oxide Possess Identical Pharmacologic Properties as Relaxants of Bovine Arterial and Venous Smooth Muscle," The Journal of Pharmacology and Experimental Therapeutics, vol. 246, No. 1, pp.

Dinh-Xuan, A. T. et al., "Non-Prostanoid Endothelium-Derived Vasoactive Factors," The Journal of International Medical Research, vol. 17, pp. 305-315 (1989).

Borland, C. D. R. et al., "A Simultaneous Single Breath Measurement of Pulmonary Diffusing Capacity with Nitric Oxide and Carbon Monoxide," The European Respiratory Journal, vol. 2, No. 1, pp. 56-63 (Jan. 1989).

Buga, G. M. et al., "Endothelium-Derived Nitric Oxide Relaxes Nonvascular Smooth Muscle," European Journal of Pharmacology, vol. 161, No. 1, pp. 61-72, (Feb. 1989).

Garg, U. C. et al., "Nitric Oxide-generating Vasodilaters and 8-Bromo-Cyclic Guanosine Monophosphate Inhibit Mitogensis and Proliferation of Cultured Rat Vascular Smooth Muscle Cells," The Journal of Clinical Investigation, vol. 83, No. 5, pp. 1774-1777 (May 1989).

Meyer, M. et al., "Nitric Oxide (NO), a New Test Gas for Study of Alveolar-capillary Diffusion," The European Respiratory Journal, vol. 2, No. 6, pp. 494-496 (Jun. 1989).

Dinh-Xuan, A. T. et al., "Primary Pulmonary Hypertension: Diagnosis, Medical and Surgical Treatment," vol. 84, pp. 189-197 (1990).

Stavert, D. M. et al., "Nitric Oxide and Nitrogen Dioxide as Inducers of Acute Pulmonary Injury When Inhaled at Relatively High Concentrations for Brief Periods," Inhalation Toxicology 2:53-67 (1990).

Moinard, J. et al., "Determination of Lung Capilary Blood Volume and Membrane Diffusing capacity in Patients with COLD using the NO-CO Method," The European Respiratory Journal, vol. 3, pp. 318-322 (1990).

Archer, S. L., "Comparison of the Hemodynamic Effects of Nitric Oxide and Endothelium-Dependent Vasodilators in Intact Lungs," Journal of Applied Physiology, vol. 68, No. 2, pp. 735-747 (Feb. 1990).

Meyer, M. et al., "Pulmonary Diffusing Capacities for Nitric Oxide and carbon Monoxide Determined by Rebreathing in Dogs," Journal of Applied Physiology, vol. 68, No. 6, pp. 2344-2357 (Jun. 1990).

Vane, J. R. et al., "Regulatory Functions of the Vascular Endothelium," The New England Journal of Medicine, vol. 323, No. 1, pp. 27-36 (Jul. 1990).

Higenbottam, T. et al., "Has the Treatment of Asthma Improved?" Chest, vol. 98, No. 3, pp. 706-712 (Sep. 1990).

Swami, A. et al., "The Pulmonary Physician and critical Care: 2. The Injury Lung: Conventional and Novel Respiratory Therapy," Thorax, vol. 47, pp. 555-562 (1992).

Bult, H. et al., "Chronic Exposure to Exogenous Nitric Oxide May Suppress its Endogenous Release and Efficacy," Journal of Cardiovascular Pharmacology, vol. 17, Suppl. 3, pp. S79-S82 (1991).

Frostell, C. et al., "Inhaled Nitric Oxide, A Selective Pulmonary Vasodilator Reversing Hypoxic Pulmonary Vasoconstriction," Circulation Journal of the American Heart Association, vol. 83, pp. 2083-2047 (1991).

Hendrickson, D.A. et al, "Regents and Stains," Manual of Clinical Microbiology, 5th Ed., American Society for Microbiology, pp. 1289-1314 (1991).

Cremona, g. et al., "Endothelium-derived Relaxing Factor and the Pulmonary Circulation," Lung, vol. 169, pp. 185-202 (1991).

Falke, K. et al., "Inhaled Nitric Oxide Selectively Reduces Pulmonary Hypertension in Severe ARDS and Improves Gas Exchange as well as right Heart Ejection fraction—A Case Report." Abstract 248. Am. Rev. Respir. Dis., vol. 143 (1991).

Fratacci, M. D., "Inhaled Nitric Oxide—A Selective Pulmonary Vasodilator of Heparin-Protamine Vasoconstriction in Sheep," Anesthesiology, vol. 75, pp. 990-999 (1991).

Denis, M., "Interferon—Gamma-treated Murine Macrophages Inhibit Growth of Tubercle Bacilli via the Generation of Reactive Nitrogen Intermediates," Cellular Immunology, vol. 132, No. 1, pp. 150-157 (Jan. 1991).

Dinh-Xuan, A. T. et al., "Impairment of Endothelium-Dependent Pulmonary-Artery Relaxation in Chronic Obstructive Lung Disease," The New England Journal of Medicine, vol. 324, No. 22, pp. 1539-1547 (May 1991).

Frostell, C. et al., "Inhaled Nitric Oxide—A Selective Pulmonary Vasodilator Reversing Hypoxic Pulmonary Vasoconstriction," Circulation, vol. 83, No. 6 (Jun. 1991).

Moncada, S. et al., "Nitric Oxide: Physiology, Pathophysiology, and Pharmacology," Pharmacological Reviews, vol. 43, No. 2 (Jun. 1991).

Frostell, C. et al., "Inhaled Nitric Oxide Dilates Human Hypoxic Pulmonary Vasoconstriction Without Causing Systemic Vasodilation," Anesthesiology, The Journal of The American Society of Anesthesiologists, Inc., vol. 75, No. 3A, Abstract A989 (Sep. 1991).

Girard, C. et al., "Inhaled Nitric Oxide (NO) in Pulmonary Hypertension Following Mitral Valve Replacement," Anesthesiology, The Journal of the American Society of Anesthesiologists, Inc., vol. 75, No. 3A, Abstract A983 (Sep. 1991).

Robert, J. D. et al., "Inhaled Nitric Oxide (NO): A Selective Pulmonary Vasodilator for the Treatment of Persistent Pulmonary Hypertension of the Newborn (PPHN)," Abstract 1279, Circulation, vol. 84, No. 4, pp. II-321 (Oct. 1991).

Pepke-Zaba, J. et al., "Inhaled Nitric Oxide as a Cause of Selective Pulmonary Vasodilatation in Pulmonary Hypertension," The Lancet, vol. 338, No. 8776, pp. 1173-1174 (Nov. 1991).

Radomski, M. W., et al., "Human Colorectal Adenocarcinoma Cells: Differential Nitric Oxide Synthesis Determines Their Ability to Aggregate Platelets," Cancer Research, vol. 51, pp. 6073-6078 (Nov. 15, 1991).

Johns, R. A., "EDRF/Nitric Oxide—The Endogenous Nitrovasodilator and a New cellular Messenger," Anesthesiology, The Journal of The American Society of Anesthesiologists, Inc., vol. 75, No. 6, pp. 927-931 (Dec. 1991).

Pearl, R. G., "The Pulmonary Circulation," Anesthesiology, vol. 5, pp. 848-854 (1992).

Chan, J. et al., "Killing of Virulent Mycobacterium Tuberculosis by Reactive Nitrogen Intermediates Produced by Activated Murine Macophages," J. Exp. Med. 175:1111-1122 (Apr. 1992).

Rossiant, R. et al., "Successful Treatment of Severe Adult Respiratory Distress Syndrome with Inhaled Nitric Oxide," American Review of Respiratory Disease, Suppl. vol. 145, No. 4, Part 2, p. A80 (Apr. 1992).

Rossiant, R. et al., "Inhaled Nitric Oxide in Contrast to Infused Prostacyclin Selectively Reduces Pulmonary Hypertension and Improves Gas Exchange in Severe ARDS," Abstract, American Review of Respiratory Disease, Suppl. vol. 145, No. 4, Part 2, p. A185.

Bigatello, L. M., "Inhaled Nitric Oxide is a Selective Pulmonary Vasodilator in Septic Patients with Severe ARDS," Abstract, American Review of Respiratory Disease, Suppl., vol. 145, No. 4, Part 2, p. A185(Apr. 1992).

Snyder, S. H. et al., Biological Roles of Nitric Oxide, Scientific American, vol. 266, No. 5, pp. 68-77 (May 1992).

Foubert, L., "Safety Guidelines for Use of Nitric Oxide," The Lancet, vol. 339, No. 8809, pp. 1615-1616 (Jun. 1992).

Messent, M. et al., "Pharmacotherapy in Lung Injury," Thorax, vol. 47, No. 7, pp. 651-656 (Jul. 1992).

Barash, P. et al. "Anesthesiology," The Journal of the American Medical Association, vol. 268, No. 3, pp. 335-337 (Jul. 1992).

Dupuy, P. M. et al., "Bronchodilator Action of Inhaled Nitric Oxide in Guinea Pigs," J. Clin. Invest., vol. 90, pp. 421-428 (Aug. 1992).

Kinsella, J. P. et al., "Hemodynamic Effects of Exogenous Nitric Oxide in Ovine Transitional Pulmonary Circulation," American Journal of Physiology: Heart and Circulatory Physiology, vol. 32, No. 3, pp. H875-H880 (Sep. 1992).

Roberts, J. D. et al., "Inhaled Nitric Oxide in Persistent Pulmonary Hypertension of the Newborn," The Lancet, vol. 340, pp. 818-819 (Oct. 1992).

Kinsella, J. P. et al., "Low-Dose Inhalational Nitric Oxide in Persistent Pulmonary Hypertension of the Newborn," The Lancet, vol. 340, pp. 819-820 (Oct. 1992).

Girard, C. et al., "Inhaled Nitric Oxide After Mitral Valve Replacement in Patients with Chronic pulmonary Artery Hypertension," Anesthesiology, The Journal of the American Society of Anesthesiologists, Inc., vol. 77, No. 5, pp. 880-883 (Nov. 1992).

Kacmarek, R. M., "Nitric Oxide as a Bronchodilator in Methacholine Induced Bronchospasm in Mild Asthmatics," Abstract (1993).

Blomqvist, H. et al., "Enhanced Pneumonia Resolution by Inhalation of Nitric Oxide?" Acta Anaesthesiol Scand, vol. 37, pp. 110-114 (1993).

Buga, G. M. et al., "Negative Feedback Regulation of Endothelial Cell Function by Nitric Oxide," Circulation Research, Journal of the American Heart Association, 73:808-812 (1993).

Higenbottam, T., "Inhaled Nitric Oxide: A Magic Bullet?" Quarterly Journal of Medicine, vol. 86, pp. 555-558 (1993).

Stenqvist, O. et al., "Evaluation of a New System for Ventilatory Administration of Nitric Oxide," Acta Anaesthesiologica Scandinavica, pp. 687-691 (1993).

Rossaint, R. et al., "Inhaled Nitric Oxide For The Adult Respiratory Distress Syndrome," New England Journal of Medicine, vol. 328, pp. 399-405 (Feb. 1993).

Maragos, C. M., et al., "Nitric Oxide/Nucleophile Complexes Inhibit the in Vitro Proliferation of A375 Melanoma Cells via Nitric Oxide Release," Cancer Research, vol. 53, pp. 564-568 (Feb. 1, 1993).

Pearl, R. G. "Inhaled Nitric Oxide—The Past, The Present and the Future," Anesthesiology, vol. 78, No. 3, pp. 413-416 (Mar. 1993).

Assreuy, J. et al., "Feedback Inhibition of Nitric Oxide Synthase Activity by Nitric Oxide," British Journal of Pharmacology, vol. 108, pp. 883-837 (Mar. 1993).

Higenbottam, T. et al., "Highlights on Pulmonary Hypertension: A Commentary," The European Respiratory Journal, vol. 6, No. 7, pp. 932-933 (Jul. 1993).

Haworth, S. G., "Pulmonary Hypertension in Childhood," The European Respiratory Journal, vol. 6, No. 7, pp. 1037-1043 (Jul. 1993).

Higenbottam, T. et al., "Acute and Chronic Hypoxic Pulmonary Hypertension," The European Respiratory Journal, vol. 6, No. 8, pp. 1207-1212 (Sep. 1993).

Mansch, R. et al., "Simulation of Microbiologically and chemically Influenced corrosion of Natural Sandstone," Abstract, ASTM Speacial Technical Publication, 203-16; 1 pg. (1994).

Lowenstein, C. J. et al., "Nitric Oxide: a Physiologic Messenger," Annals of Internal Medicine, vol. 120, Issue 3, pp. 227-237 (Feb. 1994).

Dong, Z., et al., "Inverse Correlation Between Expression of Inducible Nitric Oxide Synthase Activity and Production of Metastasis in K-1735 Murine Melanoma Cells," Cancer Research, vol. 54, pp. 789-793 (Feb. 1, 1994).

Butt, A. Y. et al., "New Therapies for Primary Pulmonary Hypertension," Chest, vol. 105, No. 2, pp. 21S-25S (Feb. 1994).

Foubert, L. et al., "Nitric Oxide in Pulmonary Hypertension: Therapeutic Considerations," Journal of Cardiothoracic and Vascular Anesthesia, vol. 8, No. 3, Suppl. 2, p. 41 (Jun. 1994).

Snow, D. et al., "Inhaled Nitric Oxide in Pulmonary Hypertension," Journal of Cardiothoracic and Vascular Anesthesia, vol. 8, No. 3, Suppl. 2, Abstract No. 127 (Jun. 1994).

O'Brien, L. et al., Strains of Mycobacterium Tuberculosis Differ in Susceptibility to Reactive Nitrogen Intermediates In Vitro, Infection and Immunity, vol. 62, No. 11, pp. 5187-5190 (Aug. 1994).

Young, J. D., "A Universal Nitric Oxide Delivery System," British Journal of Anaesthesia, vol. 73, No. 4, pp. 700-702 (Oct. 1994).

Hagenah, Jens-Uwe, "The Use of Nitric Oxide (NO) in Intensive Care Ventilation," Dragerwerk Aktiengesellscha, pp. 1 and 3-36.

Hanson, S. R., et al., "Nitric Oxide Donors: A Continuing Opportunity in Drug Design," Nitric Oxide Biochemistry, Molecular Biology, and Therapeutic Implications, Advances in Pharmacology, vol. 34, pp. 383-398 (1995).

Chan, J. et al., "Effects of Nitric Oxide Synthase Inhibitors on Murine Infection with Mycobacterium Tuberculosis," Infection and Immunity, vol. 63, No. 2., pp. 736-740 (Feb. 1995).

DeGroote, M. A., et al., "NO Inhibitions: Antimicrobial Properties of Nitric Oxide," Clinical Infectious Disease, vol. 21, Suppl. 2, pp. S162-S165 (Oct. 1995).

Body, S. C., M.D. et al., "Nitric Oxide: Delivery, Measurement, and Clinical Application," Journal of Cardiothoracic and Vascular Anesthesia, vol. 9, No. 6, pp. 748-763 (Dec. 1995).

Higenbottam, T. et al., "the Treatment of Primary Pulmonary Hypertension," Therapeutic Applications of Iloprost, A Volume in the Clinical Monograph Series, pp. 35-41 (Apr. 1995).

Szabo, C., "The Pathophysiological Role of Peroxynitrite in Shock, Inflammation and Ischemia-Reperfusion Injury," Shock, vol. 6, No. 2, pp. 79-88 (1996).

Higenbottam, T., "Nitric Oxide and the Lung," Horizons in Medicine, No. 7 pp. 203-224 (1996).

Young, J. D. et al., "Delivery and Monitoring of Inhaled Nitric Oxide," Intensive Care Medicine, vol. 22, No. 1, pp. 77-86 (Jan. 1996).

Mellgren, K., et al., "Nitric Oxide in the Oxygenator Sweep Gas Reduces Platelet Activation During Experimental Perfusion," The Annals of Thoracic Surgery, vol. 61, No. 4, pp. 1194-1198 (Apr. 1996).

Ramnarine, S. I., et al., "Nitric Oxide Inhibition of Basal and Neurogenic Mucus Secretion in Feerrete Trachea in Vitro," British Journal of Pharmacology, vol. 118 (4), pp. 998-1002 (Jun. 1996).

Channick, R. N., M.D. et al., "Pulsed Delivery of Inhaled Nitric Oxide to Patients with Primary Pulmonary Hypertension," Chest, The Cardiopulmonary and Critical Care Journal, vol. 109, No. 6, pp. 1545-1549 (Jun. 1996).

Hudome, S. M., M.D. et al., "Precise Control of Nitric Oxide Concentration in the Inspired Gas of Continuous Flow Respiratory Devices," Pediatric Pulmonology, vol. 22, No. 3, pp. 182-187 (Sep. 1996).

Cuthbertson, B. H. et al., "Inhaled Nitric Oxide," The Lancet, vol. 348, No. 9039, pp. 1447-1448 (Nov. 1996).

Gerlach, H. et al., "Low Levels of Inhaled Nitric Oxide in Acute Lung Injury," Nitric Oxide and the Lung, vol. 98, Chapter 14, pp. 271-283 (1997).

Dupuy, P. M. et al., "Bronchial Effects of Nitric Oxide," Nitric Oxide and the Lung, vol. 98, Chapter 15, pp. 285-311 (1997).

Leopold, J. A. et al., "New Developments in Nitrosovasodilator Therapy," Vascular Medicine, vol. 2, No. 3 (1997).

Rook, G. A. W., "Intractable Mycobacterial Infections Associated with Genetic Defects in the Receptor for Interferon Gamma: What Does This Tell Us About Immunity to Mycobacteria?" Thorax, vol. 52 (Suppl. 3), pp. S41-S46 (1997).

Katayama, Y. et al., "Inhaled Nitric Oxide and Arterial Oxygen Tension in Patients with chronic Obstructive Pulmonary Disease and Severe Pulmonary Hypertension," Thorax, The Journal of the British Thoracic Society, vol. 52, pp. 120-124 (1997).

Neonatal Inhaled Nitric Oxide Study Group, "Inhaled Nitric Oxide in Full-Term and Nearly Full-Term Infants with Hypoxic Respiratory Failure," New England Journal of Medicine, 336(9):597-604 (Feb. 1997).

Roberts, J. D. et al., "Inhaled Nitric Oxide and Persistent Pulmonary Hypertension of the Newborn," New England Journal of Medicine, 336:605-610 (Feb. 1997).

Imanaka, H., M.D. et al., "Inaccuracies of Nitric Oxide Delivery Systems During Adult Mechanical Ventilation," Anesthesiology, vol. 86, No. 3, pp. 676-688 (Mar. 1997).

Marriott, H. et al., "The Role of Nitric Oxide in Respiratory Disease," Schweiz Med Wochenschr, vol. 127, pp. 709-714 (Apr. 1997).

Nozaki, Y. et al., "Mechanism of Nitric Oxide-Dependent Killing of Mycobacterium bovis BCG in Human Alveolar Macrophages," Infection and Immunity, vol. 65, pp. 3644-3647 (Sep. 1997).

Hess, D., RRT, Ph.D. et al., "Delivery Systems for Inhaled Nitric Oxide," Respiratory Care Clinics of North America, vol. 3, No. 3, pp. 371-410 (Sep. 1997).

Hoehn T., M.D. et al., "Effect of Therapeutic Concentrations of Nitric Oxide on Bacterial Grown in Vitro," Crit Care Med, vol. 26, No. 11, pp. 1857-1862 (1998).

Bauer, J. A. et al., Evaluation of Linear Polyethylenei-mine/Nitric Oxide Adduct on Wound Repair: Therapy Versus Toxicity, The Wound Healing Society, pp. 569-577 (1998).

Pizzichini, M. M. M. et al., "Asthma and Natural Colds: Inflammatory Indices in Induced Sputum: A Feasibility Study," American Journal of Respiratory Critical Care Medicine, vol. 158, pp. 1178-1184 (1998).

Higenbottam, T. et al., "Primary and Secondary Pulmonary Hypertension," Seminars in Respiratory and Critical Care Medicine, vol. 19, No. 1, pp. 91-95 (1998).

Long R. et al., "Pulmonary Tuberculosis Treated with Directly Observed Therapy: Serial Changes in Lung Structure and Function," Chest, vol. 113, pp. 933-943 (1998).

Klein, M.D. et al., "Nitric Oxide Delivery Systems," Acta Anaesthesiologica Scandinavica, pp. 274-275 (1998).

Francoe, M, RRT et al., "Inhaled Nitric Oxide: Technical Aspects of Administration and Monitoring," Critical Care Medicine, vol. 26, No. 4, pp. 782-796 (Apr. 1998).

Keefer, L. K., "Nitric Oxide-Releasing Compounds: From Basic Research to Promising Drugs," The American Chemical Society, vol. 28, pp. 30-35 (Aug. 1998).

Ivy, D. D., M.D. et al., "Acute Hemodynamic Effects of Pulsed Delivery of Low Flow Nasal Nitric Oxide in Children with Pulmonary Hypertension," The Journal of Pediatrics, vol. 133, No. 3, pp. 453-456 (Sep. 1998).

Hiesmayr, M. J. et al., "Performance of Proportional and Continous Nitric Oxide Delivery Systems During Pressure- and Volume-Controlled Ventilation," The British Journal of Anaesthesia, vol. 81, No. 4, pp. 544-552 (Oct. 1998).

Katayama, Y., M.D. et al., "Minimizing the Inhaled Dose of NO With Breath-by-Breath Delivery of Spikes of Concentrated Gas," Circulation, Journal of the American Heart Association, vol. 98, No. 22 (Dec. 1998).

Higenbottam, T. et al., "Treatments for Severe Pulmonary Hypertension," The Lancet, vol. 353, No. 9150, pp. 338-340 (Jan. 1999).

Long, R. et al., "Mycobacteriocidal Action of Exogenous Nitric Oxide," Antimicrobial Agents and Chemotherapy, vol. 43, No. 2, pp. 403-405, (Feb. 1999).

Schofnagl, H. et al., "Proportional and Continuous NO Delivery Systems," British Journal of Anaesthesia, vol. 82, No. 4, pp. 647-653 (Apr. 1999).

Rimmelzwaan, G. F. et al., "Inhibition of Influenza Virus Replication by Nitric Oxide," Journal of Virology, American Society for Microbiology, vol. 73, No. 10, pp. 8880-8883 (Oct. 1999).

Webert, K. E., M.D. et al., "Effects of Inhaled Nitric Oxide In A Rate Model of *Pseudomonas ceruginosa* Pneumonia," Crit Car Med, vol. 28, No. 7, pp. 2397-2405 (2000).

Tamaoki, J., M.D., et al., "Impairment of Airway Mucociliary Transport in Patients with Sinobronchial Syndrome: Role of Nitric Oxide," Journal of Aerosol Medicine, vol. 13, No. 3, pp. 239-244 (Nov. 2000).

Long et al., "Treatment of Sputum-Smear Positive Pulmonary Tuberculosis With Inhaled Nitric Oxide," 2001-Abstract Form to the ATS 2001 San Francisco, May 18-23, 2001 (faxed Mar. 27, 2001).

Frank, S., et al., "Nitric Oxide Drives Skin Repair: Novel Functions Of An Established Mediator," Kidney International, vol. 61, pp. 882-888 (2002).

Imada, M., et al., "Functional Roles of Nasal Nitric Oxide in Nasal Patency and Mucociliary Function," ACTA Oto-Laryngologica, vol. 122, No. 5, pp. 513-519 (Jul. 2002).

Kirov, M. Y., M.D., et al., "Combination of Intravenously Infused Methylene Blue and Inhaled Nitric Oxide Ameliorates Endotoxin-Induced Lung Injury in Awake Sheep," Critical Care Medicine, vol. 31, No. 1, pp. 179-186 (Jan. 2003).

Shami, P. J., et al., JS-K, A Glutathione/Glutathione S-Transferase-activated Nitric Oxide Donor of the Diazeniumdiolate Class with Potent Antineoplastic Activity, Molecular Cancer Therapeutics, vol. 2, pp. 409-417 (Apr. 2003).

Counter-Defendants's First Amended Responses to Counterclaimants's Second Set of Interrogatories Relating to Counterclaims (Nos. 19-38) (Oct. 2003).

Miller, Chris C. et al.; "Treatment of Chronic Nonhealing Leg Ulceration with Gaseous Nitric Oxide: A Case Study"; Journal of Cutaneous Medicine and Surgery, pp. 233-238 (2004).

Vijh, A. K., "High Infectious Burden, Low Cancer Incidence, and Early Malignancy in Developing Countries: A Molecular Hypothesis in Term of the Role of Nitric Oxide," Medical Hypotheses, vol. 63, pp. 208-210 (Feb. 2004).

Sanders, S. P. et al., "Role of Nasal Nitric Oxide in the Resolution of Experimental Rhinovirus Infection," Journal of Allergy and Clinical Immunology, vol. 113, No. 4, pp. 697-702 (Apr. 2004).

Schmidt, I. et al., Physiologic and Proteomic Evidence for a Role of Nitric Oxide in Biofilm Formation by *Nitrosomonas europaea* and Other Ammonia Oxidizers; Journal of Bacteriology, vol. 186, No. 9, pp. 2781-2788 (May 2004).

Reynolds, M. M., et al., "Nitric Oxide-Releasing Hydrophobic Polymers: Preparation, Characterization, and Potential Biomedical Applications," Free Radical Biology & Medicine, The Official Journal for the Society for Free Radical Biology and Medicine, vol. 37, No. 7, pp. 926-936 (Oct. 2004).

Lechner, M., et al., "Inducible Nitric Oxide Synthase (iNOS) in Tumor Biology: The Two Sides of the Same Coin," Seminars in Cancer Biology, vol. 15, pp. 277-289 (2005).

Ghaffair, A., et al., "A Direct Nitric Oxide Gas Delivery System for Bacterial and Mammalian Cell Cultures," Nitric Oxide Biology and Chemistry, vol. 12, pp. 129-140 (2005).

Proud, D., "Nitric Oxide and The Common Cold," Journal of Allergy and Clinical Immunology, vol. 5, pp. 37-42 (2005).

Nablo, B. J., Inhibition of Implant-Associated Infections Via Nitric Oxide Release, Science Direct, Biomaterials, vol. 26, pp. 6984-6990 (May 2005).

McMullin, B. B., MSc RRT, et al., "The Antimicrobial Effect of Nitric Oxide on the Bacteria That Cause Nosocomial Pneumonia in Mechanically Ventilated Patients in the Intensive Care Unit," Respiratory Care, vol. 50, No. 11, pp. 1451-1456 (Nov. 2005).

Hurford, W. E.; Nitric Oxide As A Bacterial Agent: Is The Cure Worse Than The Disease?; Respiratory Care, vol. 50, No. 11, pp. 1428-1429 (Nov. 2005).

Katayama, Y. et al., "A Minimal Dose of Inhaled Nitric Oxide Delivered As A 'Spike 'of Small Volume in Early Inhalation," Section of Respiratory Medicine, Division of Clinical Sciences, The Medical School, University of Sheffield (23 pages).

Turchi, J. J., "Nitric Oxide and Cisplatin Resistance: NO Easy Answers," PNAS, vol. 103, No. 12, pp. 4337-4338 (Mar. 21, 2006).

* cited by examiner

USE OF NITRIC OXIDE GAS IN AN EXTRACORPOREAL CIRCUITRY TO TREAT BLOOD PLASMA

PRIORITY CLAIM

This application is a continuation-in-part application of and claims priority to U.S. application Ser. No. 10/658,665, filed on Sep. 9, 2003, which claims priority to U.S. Provisional Application No. 60/409,400, filed on Sep. 10, 2002. Both applications are herein incorporated by reference in their entirety.

FIELD

The present invention is directed to providing nitric oxide containing gas to mammals for medical applications.

BACKGROUND

Numerous techniques have been developed for circulating the blood of a patient outside the body in an "extracorporeal" circuit and then returning it to the patient. For example, in dialysis for patients with kidney failure, blood is circulated extracorporeally and contacted with a large membrane surface separating the blood from a dialysate solution, and urea and other blood chemicals are migrated across the membrane to cleanse the blood, which is then returned to the patient. Another example of extracorporeal circulation is cardiopulmonary bypass ("CPB"), the procedure of mechanically bypassing both the heart and lungs to allow the whole heart to be isolated for surgical repair.

Several complications may arise in circulating blood outside of the patient's body. For example, contact of the blood with the foreign surfaces of the extracorporeal circuit triggers a massive defense reaction in blood proteins and cells that has been called "the whole body inflammatory response." U.S. Pat. No. 5,957,880, herein incorporated by reference in its entirety, describes an improvement in extracorporeal circulation that employs contacting nitric oxide gas with the circulating blood. The nitric oxide gas was found to inhibit activation of blood platelets, thereby effecting a reduction or prevention of the whole body inflammation response heretofore associated with use of such apparatus.

In the 1980's, it was discovered by researchers that the endothelium tissue of the human body produced nitric oxide (NO), and that NO is an endogenous vasodilator, namely, an agent that widens the internal diameter of blood vessels. Since this discovery, numerous medical applications of NO have developed. Researchers have discovered that inhaled NO may be used to treat various pulmonary diseases in patients. For example, NO has been investigated for the treatment of patients with increased airway resistance as a result of emphysema, chronic bronchitis, asthma, adult respiratory distress syndrome (ARDS), and chronic obstructive pulmonary disease (COPD).

NO has also been investigated for its use as a sterilizing agent. It has been discovered that NO will interfere with or kill the growth of bacteria grown in vitro. PCT International Application No. PCT/CA99/01123 published Jun. 2, 2000 discloses a method and apparatus for the treatment of respiratory infections by NO inhalation. NO has been found to have either an inhibitory and/or a cidal effect on pathogenic cells. Delivery of the nitric oxide in the gaseous phase is preferably through a device having a specially designed nasal-cannula or a mask having a modified Fruman valve. Nitric oxide containing gas has been administered topically to treat infected tissue on the skin surface. In U.S. Pat. No. 6,432,077, Stenzler teaches that topical application of nitric oxide to wounds and/or skin of mammals is beneficial to wound healing because the nitric oxide decreases further infection. In U.S. Pat. No. 6,793,644, Stenzler describes a method of bathing the infected tissue with nitric oxide containing gas, while providing for effective evacuation of the nitric oxide containing gas from the area surrounding the infected tissue.

NO has been investigated as an agent against pathogens and microorganisms, such as viruses, bacteria, mycobateria, parasites, and fungi. Nitric oxide has found utility as a bactericidal agent. Additionally, several researchers have documented the antiviral effects of NO. Cells infected with influenza virus A/Netherlands/18/94 were treated with NO, an experiment described in Rimmelzwaan, et. al., "Inhibition of Influenza Virus Replication by Nitric Oxide," J. Virol. 1999; 73:8880-83, herein incorporated by reference in its entirety. Results show the effectiveness of NO as a preventive therapy to viral agents. Additionally, a study by Sanders, et. al. demonstrates the effectiveness of NO as an antiviral agent, particularly against human rhinovirus. See Sanders, et. al., "Role of Nasal Nitric Oxide in the Resolution of Experimental Rhinovirus Infection," J. Allergy Clin, Immunol. 2004 April; 113(4):697-702, herein incorporated by reference in its entirety.

U.S. patent application Ser. No. 10/658,655 describes a method for systematic delivery of the nitric oxide moiety in an extracorporeal circuit to reduce whole body contamination by pathogenic or toxic substances. Specific applications of the Ser. No. 10/658,655 application focus on managing bacteremia (blood poisoning) and/or septicemia in mammals. The Ser. No. 10/658,655 application describes the method of reducing pathogens in the mammal's blood stream to include the steps of: (1) providing an extracorporeal blood circuit; (2) circulating the mammal's blood through the extracorporeal blood circuit; and (3) exposing the blood in the circuit with nitric oxide gas in a concentration sufficient to reduce pathogenic content in the blood.

Accordingly, there is a need for a device and method for the extracorporeal treatment of the blood by the administration of nitric oxide containing gas. The exposure to NO containing gas could be used in combination with other extracorporeal procedures such as dialysis to provide for a defense against infections or as a stand alone method for decontamination and/or treatment of the blood. The treatment serves to effectively contact the blood with the nitric oxide containing gas so as to reduce the concentration of pathogens in the blood. The methods consider how to best contact the pathogens in the blood. The methods consider how to remove dissolved nitric oxide gas from the treated blood so that the blood returned to the patient has a safe concentration of dissolved nitric oxide gas therein.

SUMMARY OF THE INVENTION

One embodiment of the present invention is a method of reducing pathogens in the blood of a mammal. The method includes the steps of: (1) obtaining blood from a mammal or a blood source; (2) separating the blood into plasma and blood cells; (3) exposing the plasma to nitric oxide containing gas; (4) combining the exposed plasma with the blood cells; (5) reducing nitric oxide content in the recombined blood; and (6) returning the blood to the mammal or blood source.

The content of nitric oxide in the recombined blood may be reduced by contacting the combined blood with a gaseous source, wherein the gaseous source has a nitric oxide content that is less than the combined blood. Such a gas source is ambient air. The content of nitric oxide in the combined blood may be reduced by providing a semipermeable membrane selectively permeable to nitric oxide gas in between the combined blood and a gaseous source. The content of nitric oxide in the combined blood may be reduced by exposing the blood to a composition comprising a free radical scavenger.

The methods of the present invention may also include the step of exposing the blood to oxygen.

The separation step may be accomplished with known plasmapheresis techniques. These techniques include a filter, a centrifuge, and dialysis to separate the blood cells from the plasma or serum.

The methods of the present invention may use a nitric oxide containing gas having a nitric oxide concentration of about 120 ppm to about 400 ppm, preferably, about 160 ppm to about 220 ppm. These concentrations combined with sufficient time and contact with the plasma reduce pathogen concentration in the plasma. Exposure of the plasma to the nitric oxide containing gas effectively kills viruses, bacteria, mycobateria, parasites, and fungi found in the plasma.

The plasma absorbs nitric oxide gas through an effective exposure system. One such system includes providing a semipermeable membrane selectively permeable to nitric oxide gas and impermeable to nitrogen gas. The plasma contacts the outside membrane. The nitric oxide containing gas is delivered to the inside of the membrane under pressure sufficient to drive the nitric oxide across the membrane for contact with the plasma on the outside of the membrane.

Another embodiment of the invention is an extracorporeal blood circuit capable of completing the method steps outlined above. The extracorporeal blood circuit includes: (1) an inlet line adapted to receive blood from a mammal or a blood source; (2) an outlet line adapted to return blood to the mammal or blood source; (3) a fluid circuit for fluid communication between the inlet and the outlet line, wherein the fluid circuit comprises: (a) at least one pump acting on the fluid circuit to circulate the blood therethrough; (b) a separation unit in fluid communication with the inlet line, wherein the separation unit is adapted to separate the blood received from the mammal or source into plasma and blood cells; (c) a nitric oxide unit that exposes the plasma with a nitric oxide gas containing gas; (d) a mixer for combining the exposed plasma with the blood cells; and (e) a reduction unit for reducing the nitric oxide content in the combined blood, wherein the reduction unit is in fluid communication with the outlet line.

Other units in the circuitry may include one or more of a reservoir to collect the blood from the mammal or source, an oxygenator, a dialysis component, an organ perfusion component, a heat exchange component, and an oxygenation component.

Thus, the exposure of the blood to nitric oxide containing gas provides a modality in the medical management of bacteremia (blood poisoning) and/or septicemia in mammals.

DETAILED DESCRIPTION OF THE PREFERRED EMBODIMENTS

Before the present compositions and methods are described, it is to be understood that this invention is not limited to the particular devices, compositions, methodologies or protocols described, as these may vary. It is also to be understood that the terminology used in the description is for the purpose of describing the particular versions or embodiments only, and is not intended to limit the scope of the present invention which will be limited only by the appended claims.

Although any methods, devices, and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention. As used herein, terms such as "subject," "patient," and "mammal" may be used interchangeable.

Figure 1:
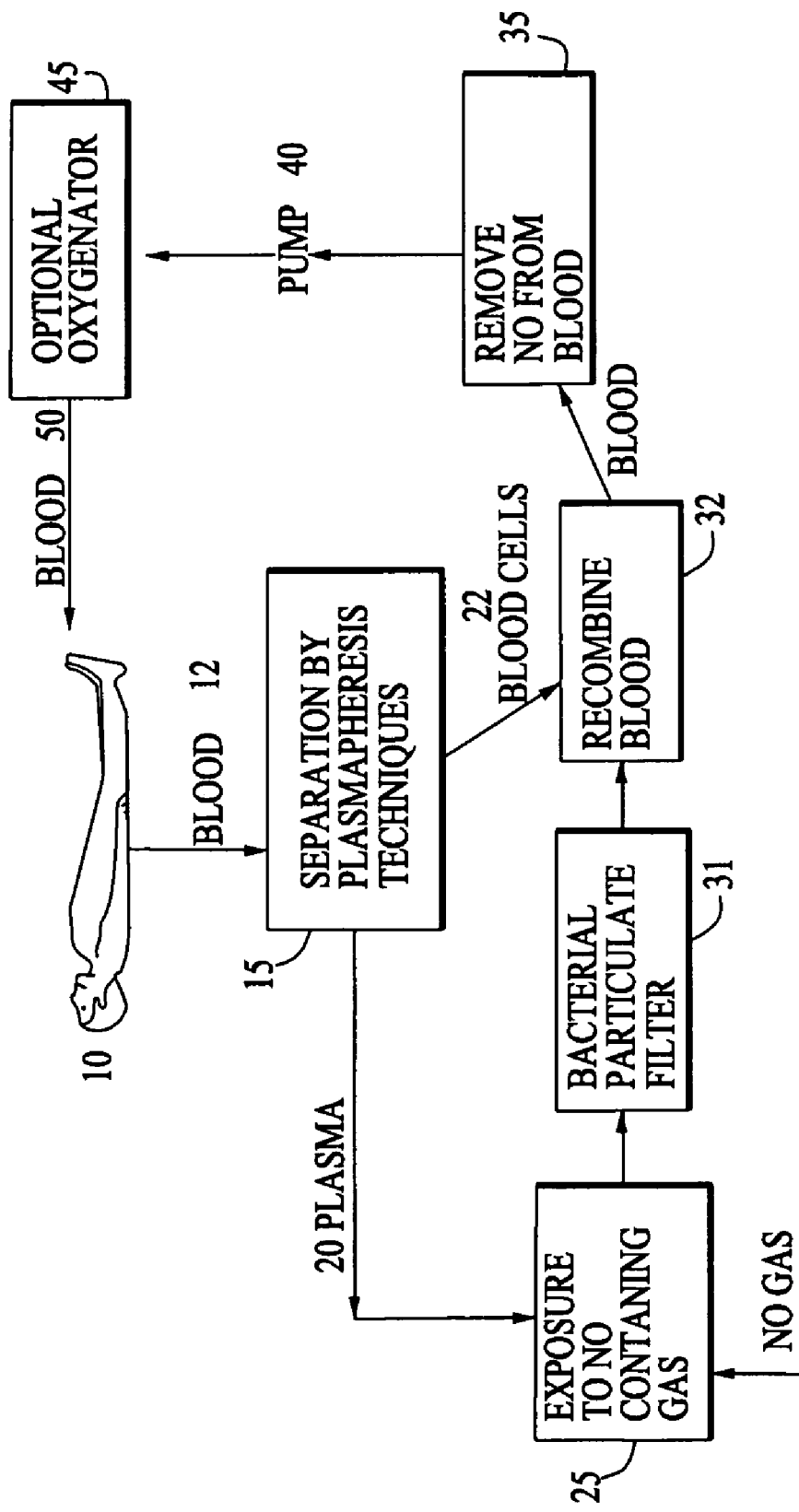
FIG. 1 is a flow chart of a method of reducing pathogens in blood, according to an embodiment of the invention.

FIG. 1 represents a flow chart for a method of extracorporeal treatment of the blood. At step 12, blood is extracted from a patient 10 or blood source. For ease of description, the Applicants have focused on extraction from a human patient. However, the methods and devices are applicable to other mammals and may also be used to treat blood from any source, such as a blood bank. Any appropriate inlet line may be used to extract blood from a patient. For example, extraction may include inserting one or more venous catheter into the patient, either in a limb or central vein. Blood may be collected into an optional reservoir and then routed to the separator or blood may flow directly into the separator.

Next, at step 15, the extracted blood is separated into blood's two main components, i.e., the plasma or serum and the blood cells, including both red and white blood cells. This step may also be thought of as the removal of blood cells from the plasma. Several techniques may be used to separate blood into plasma 20 and blood cells 22. Such techniques may be borrowed from plasmapheresis techniques. Plasmapheresis is a blood purification procedure also known as plasma exchange. In plasmapheresis, blood is removed from a patient, blood cells are separated from plasma, fresh plasma is substituted for the extracted plasma, and the fresh plasma and blood cells are returned the patient. The present methods thus rely on the principles of separation exhibited in plasmapheresis techniques. These separation techniques include filtration, dialysis and centrifugation.

For example, in discontinuous flow centrifugation, about 300 mL of blood is centrifuged at a time to separate plasma from blood cells. In discontinuous flow, only one venous catheter line is required. Blood may be routed from the patient to a collection reservoir before batch configuration. A continuous flow centrifugation may also be practiced using two or more venous lines. This continuous procedure requires slightly less blood volume to be out of the patient at any one time. In plasma filtration, two venous line are used. The plasma is filtered out of the blood using standard hemodialysis equipment. Less than 100 mL of blood are required to be outside the patient at one time using this filtering technique.

Once plasma has been isolated from the blood, it may be exposed to nitric oxide containing gas, at step 25. As described in the background section, nitric oxide gas has been used against pathogens, such as viruses, bacteria, mycobateria, parasites, and fungi. These pathogens, if blood borne, may be found in the patient's plasma or serum. To more effectively target the destruction of pathogens in a patient's blood, the isolated plasma is exposed to nitric oxide containing gas. This direct exposure of the plasma to a nitric oxide containing gas, as compared to blood (plasma and blood cells) is a highly effective decontamination technique.

At step 25, exposing the plasma to a nitric oxide containing gas may be accomplished using the techniques described in the parent application, U.S. patent application Ser. No. 10/658,665, herein incorporated in its entirety. The nitric oxide containing gas may be supplied at step 30. Appropriate techniques for diluting nitric oxide gas to usable concentrations may be employed, such as appropriate blending of pure nitric oxide with other carrier gases. Carrier gases may include air, nitrogen, and oxygen. The methods of the present invention may use a nitric oxide containing gas having a nitric oxide concentration of about 120 ppm to about 400 ppm, preferably, about 160 ppm to about 220 ppm.

Figure 4:
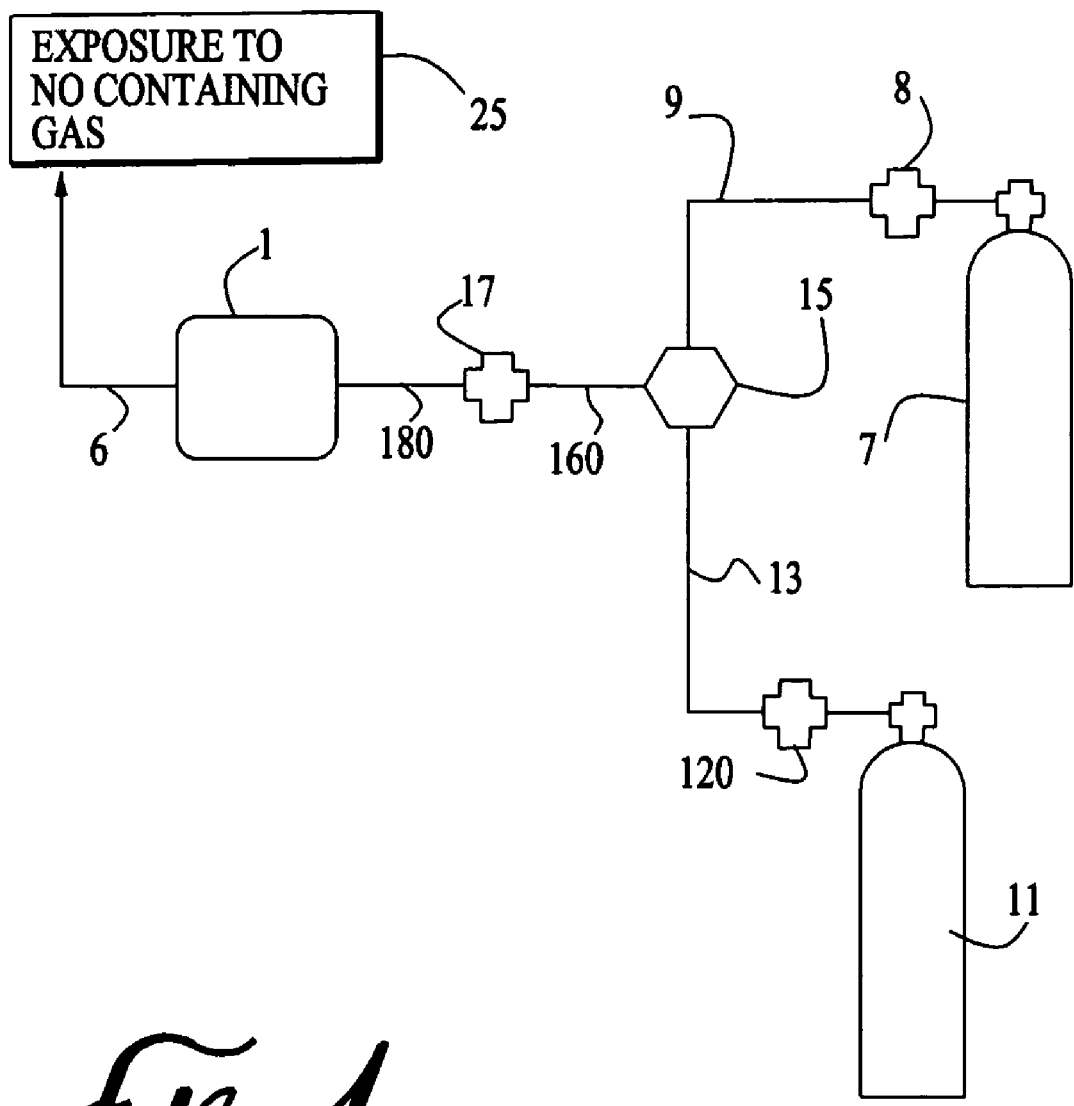
FIG. 4 is a schematic showing the nitric oxide source and delivery.

The nitric oxide containing gas may be dosed and delivered using known delivery techniques. See FIG. 4, wherein a schematic is shown demonstrating one manner of delivery of NO gas. The nitric oxide (NO) source 7, can be a pressurized cylinder containing nitric oxide (NO) gas, and a nitric oxide flow control valve/pressure regulator 8, delivering nitric oxide (NO) to the gaseous nitric oxide delivery device 1 through supply tubing 9 and an optional gas blender 15. In FIG. 4, the nitric oxide (NO) gas source 7 is a pressurized cylinder containing nitric oxide (NO) gas. While the use of a pressurized cylinder is the preferable method of storing the nitric oxide (NO) containing gas source 7, other storage and delivery means, such as a dedicated feed line can also be used. Typically the nitric oxide (NO) gas source 7 is a mixture of $N_2$ and NO. While $N_2$ is typically used to dilute the concentration of NO within the pressurized cylinder, any inert gas can also be used.

When the NO gas source 7 is stored in a pressurized cylinder, it is preferable that the concentration of NO in the pressurized cylinder fall within the range of about 800 ppm to about 1200 ppm. Commercial nitric oxide manufacturers typically produce nitric oxide mixtures for medical use at around the 1000 ppm range. Extremely high concentrations of NO are undesirable because accidental leakage of NO gas is more hazardous, and high partial pressures of NO tends to cause the spontaneous degradation of NO into nitrogen. Pressurized cylinders containing low concentrations of NO (i.e., less than 100 ppm NO) can also be used in accordance the device and method disclosed herein. Of course, the lower the concentration of NO used, the more often the pressurized cylinders will need replacement.

FIG. 4 also shows source of diluent gas 11 as part of the NO delivery device 1 that is used to dilute the concentration of nitric oxide (NO) for delivery to the gaseous nitric oxide (NO) delivery device 1 through line 13. The source of diluent gas 11 can contain $N_2$, $O_2$, air, an inert gas, or a mixture of these gases. It is preferable to use a gas such as $N_2$ or an inert gas to dilute the NO concentration since these gases will not oxidize the nitric oxide (NO) into $NO_2$, as would $O_2$ or air. The source of diluent gas 11 is shown as being stored within a pressurized cylinder. While the use of a pressurized cylinder is shown in FIG. 4 as the means for storing the source of diluent gas 11, other storage and delivery means, such as a dedicated feed line can also be used. The nitric oxide (NO) gas from the nitric oxide (NO) gas source 7 and the diluent gas from the diluent gas source 11 preferably pass through flow control valve/pressure regulators 8, 120, to reduce the pressure of gas that is admitted to the gaseous nitric oxide (NO) delivery device 1.

The respective gas streams pass via tubing 9, 13, to an optional gas blender 15. The gas blender 15 mixes the nitric oxide (NO) gas and the diluent gas to produce a nitric oxide (NO)-containing gas that has a reduced concentration of nitric oxide (NO). Preferably, the nitric oxide (NO)-containing gas that is output from the gas blender 15 has a concentration that is greater than about 100 ppm. The nitric oxide (NO)-containing gas that is output from the gas blender 15 travels via tubing 160 to a flow control valve 17. The flow control valve 17 can include, for example, a proportional control valve that opens (or closes) in a progressively increasing (or decreasing if closing) manner. As another example, the flow control valve 17 can include a mass flow controller. The flow control valve 17 controls the flow rate of the nitric oxide (No)-containing gas that is input to the gaseous nitric oxide (NO) delivery device 1. The nitric oxide (NO)-containing gas leaves the flow control valve 17 via flexible tubing 180. The flexible tubing 180 attaches to an inlet of the gaseous nitric oxide (NO) delivery device 1. The inlet for 1 might include an optional one-way valve that prevents the backflow of gas. From flexible tubing 6, the NO containing gas is routed to unit 25 (FIG. 1), wherein the plasma is exposed to the gas.

An effective amount, i.e., an amount sufficient to reduce the content of pathogens in the plasma, is generally greater than about 100 ppm nitric oxide gas. A flowrate of about 1 liter per minute of about 160 ppm nitric oxide to about 400 ppm nitric oxide may be delivered to the exposure unit. The nitric oxide containing gas is controllably delivered in relation to the amount of plasma being treated.

A semipermeable membrane selectively permeable to nitric oxide gas and impermeable to nitrogen gas may provide an effective exposure technique at step 25 (FIG. 1). The outside of the membrane contacts the plasma, while the inside of the membrane provides the interface for the nitric oxide containing gas. The nitric oxide containing gas is delivered to the inside of the membrane under pressure sufficient to drive the nitric oxide across the membrane, contacting the plasma of the other side. Such contact may be accomplished with the diffusion device illustrated in FIG. 2.

Figure 2:
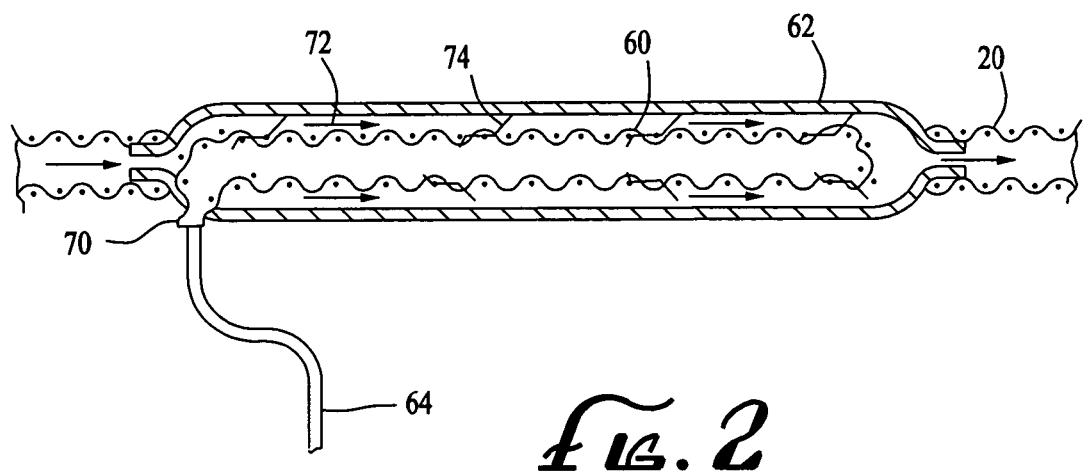
FIG. 2 is a schematic of a diffusion conduit through which the nitric oxide containing gas may contact the plasma, according one embodiment of the invention.

Referring to FIG. 2, the gas permeable membrane 60 is elongated and tubular in form and is disposed longitudinally within conduit 62 adapted to come into contact with plasma flowing through the diffusion conduit 62. The nitric oxide containing gas is supplied through tubing 64 and flows into the interior of gas permeable membrane 60. Due to the permeability of this membrane 60 to nitric oxide gas, the gas will diffuse through the membrane and dissolve in the plasma where it will come in contact with pathogens. The membrane 60 is selected to be impermeable to the carrier gas, such as nitrogen or air and thus the carrier gas will not diffuse through the membrane. The nitric oxide containing gas flows into the membrane 60 at location 70. As the gas pressure inside the gas permeable membrane 60 exceeds the pressure of the plasma within conduit 62, nitric oxide gas will diffuse from the membrane into the plasma as indicated by arrows 74. The plasma flows through the diffusion conduit 62 as illustrated by arrows 72.

Before recombining the treated plasma and the blood cells at step 32, the treated plasma may optionally be run through a bacterial particulate filter to remove lipopolysaccharide (LPS) material, at step 31. LPS is a result of dead bacteria as their cell walls are made up of this material. Excessive levels of LPS may cause an inflammatory response once the recombined blood is returned to the body, even if the bacteria in the plasma are dead. The line before the filter step 31 may also have a LPS monitor (not illustrated) to determine if the removal through filter step 31 is necessary. Thus, LPS is preferably removed before combining the treated plasma with the blood cells.

At step 32, the treated plasma and the blood cells are recombined in any suitable manner. Plasmapheresis techniques of recombining plasma and blood cells may be specifically employed. Therefore, the blood after the recombining step 32 contains dissolved nitric oxide gas. As explained in U.S. patent application Ser. No. 10/658,665, it may be desirable to remove some of the dissolve nitric gas in the blood before returning the blood to the patient. This removal of dissolved nitric oxide gas would specifically remove freely available (excess) nitric oxide gas remaining in the blood after treatment step 25. Much of the nitric oxide gas absorbed by the plasma at step 25 specifically binds to the pathogens to effectuate their destruction. However, excess dissolved nitric oxide gas may remain.

Such removal at step 35 may be accomplished through the use of a free radical scavenger, as described in U.S. patent application Ser. No. 10/658,665. An example of a free radical scavenger is citric acid. Removal of some of the nitric oxide gas in the blood counteracts the formation of methemoglobin in the blood. Sufficient quantities of methemoglobin may cause patient injury or death. When blood is exposed to such levels of nitric oxide gas that may reduce pathogens in the blood, the blood is ripe for the formation of methemoglobin. To counteract the formation of methemoglobin in the blood due to extracorporeal treatment, removal of some dissolved nitric oxide gas in the blood 35 is critical before its return to the patient. This removal step preferably results in treating the recombined blood to obtain levels of methemoglobin of less than about 5% and preferably less than about 2%. Methemogloblin may be measured by removing blood samples and analyzing them on a blood coximeter (spectrophotometeric techniques) or directly in the patient by using non-invasive methemoglobiomitry.

Therefore, unit 35 (FIG. 1) may be a free-radical scavenger unit containing any conventional free-radical scavenger. An example of such a conventional free-radical scavenger includes and is not limited to citric acid. In any case, the free-radical scavenger is exposed to the treated blood and cleanses the blood of residual nitric oxide, obviously, the nitric oxide is not entirely removed from the blood but it is sufficiently removed that it should not pose an obstacle to the patient's health.

Other removal techniques are possible. For example, the blood containing dissolved nitric oxide gas may be exposed to a gaseous source, wherein the gaseous source is substantially free of nitric oxide. The gaseous source has a concentration of nitric oxide that is less than the concentration of nitric oxide in the blood. Therefore, a partial pressure separation may occur. The pressure differential between the blood and the gaseous source will drive the nitric oxide gas from the blood to the gaseous source until an equilibrium of partial pressure is reached. The gaseous source may be simply ambient air. A semipermeable membrane selectively permeable to nitric oxide gas may be provided in between the blood containing the dissolved nitric oxide and gaseous source. Through passive diffusion, the higher concentration or partial pressure of nitric oxide in the liquid (blood) will pass from a region of higher concentration (blood) to a region of lower concentration (gaseous source) until a balanced partial pressure is achieved. After the diffusion of the dissolved nitric oxide gas through the membrane, the post-treatment blood would contain very little dissolved nitric oxide gas. The blood may then be safely returned to the patient, at step 50, the returned blood having this reduced nitric oxide level. The blood returned at step 50 has a reduced pathogen concentration as compared to the extracted blood 12.

Figure 3:
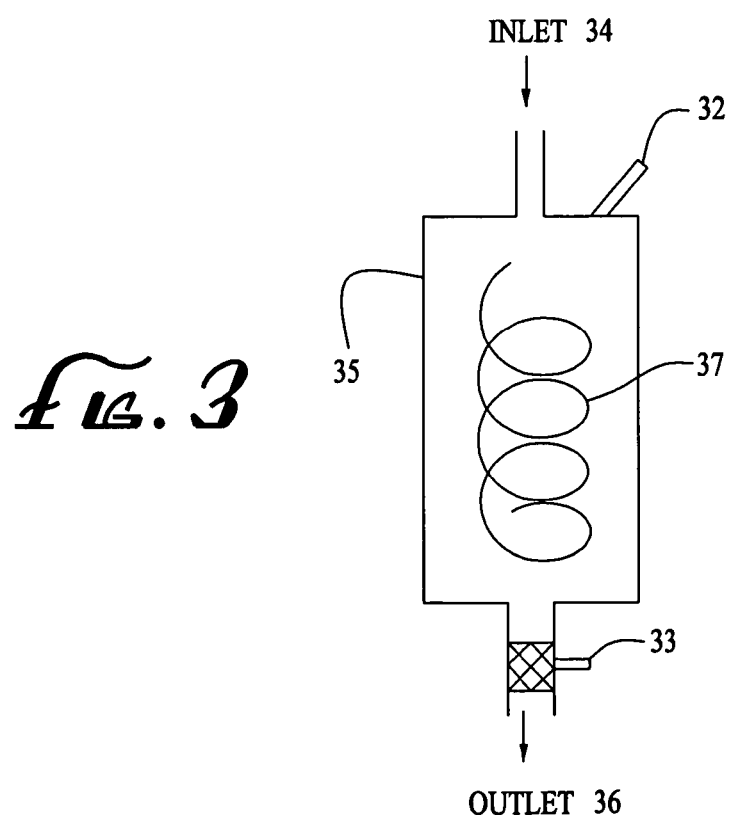
FIG. 3 is a schematic of a reduction unit, wherein the level of nitric oxide gas is reduced from the recombined blood.

As another example of the removal step 35, see FIG. 3 which is a NO reduction device with an inlet 34 for the recombined and NO-rich blood and an outlet 36 for the blood with reduced levels of NO. Essentially, it is a mixing chamber wherein citric acid or methelyne blue is titrated (feed back based on result of methemoglobin level) into the blood and mixed (spiral line 37 indicates mixing) to remove NO from plasma and/or hemoglobin. Successful removal of NO is indirectly assessed by sampling the resulting mixture (after sufficient time and mixing) from the valve 33 and measuring methmoglobin level with cooximetry inline or offline sampling.

The extracorporeal circuitry may include one or more pumps 40 necessary to transport the blood from one step to the next, before return to the patient. Additionally illustrated in FIG. 1 at step 45 is an optional oxygenator, such as the one described in U.S. patent application Ser. No. 10/658,665 used to expose the blood to oxygen gas. The oxygenator may treat the blood before it has been separated into the plasma and blood cells. Alternatively, the oxygenator may be downstream from the separation unit, such as located after the recombination of the treated plasma and the blood cells.

The extracorporeal circuitry may include: (1) an inlet line adapted to receive blood from a mammal or a blood source; (2) an outlet line adapted to return blood to the mammal or blood source; and (3) a fluid circuit for fluid communication between the inlet and the outlet line. Other components of the fluid circuit include: (1) at least one pump to circulate the blood; (2) a separation unit in fluid communication with the inlet line, wherein the separation unit is adapted to separate the blood received from the mammal or source into plasma and blood cells; (3) a nitric oxide unit that exposes the plasma with a nitric oxide gas containing gas; (4) a mixer for combining the exposed plasma with the blood cells; and (5) a reduction unit for reducing the nitric oxide content in the combined blood, wherein the reduction unit is in fluid communication with the outlet line.

Several optional components may be included into the circuitry. For example, a reservoir may be used to collect the blood from the mammal or source and thus monitor the amount of blood entering the separation unit. Additionally, in accordance with traditional uses of extracorporeal equipment and procedures, an oxygenator, a dialysis component, an organ perfusion component, a heat exchange component, and/or an oxygenation component may be incorporated into the circuitry. Such devices are known in the art. Optionally, blood circulating through the circuitry may be treated with an anticlotting agent to prevent clotting. Furthermore, the circuitry includes the necessary flexible tubing and pump devices for circulating the fluids.

While embodiments of the present invention have been shown and described, various modifications may be made without departing from the scope of the invention. The invention, therefore, should not be limited, except to the following claims, and their equivalents.

What is claimed is:

1. A method of reducing pathogens in blood, the method comprising:
   obtaining blood from a mammal or a blood source;
   separating the blood into plasma and blood cells;
   exposing the plasma to nitric oxide containing gas;
   combining the exposed plasma with the blood cells;
   reducing nitric oxide gas content in the recombined blood
      by contacting the recombined blood with a gaseous source having a nitric oxide content that is less than the recombined blood; and returning the recombined blood to the mammal or blood source.

2. The method of claim 1, wherein the gaseous source is ambient air.

3. The method of claim 1, further comprising exposing the blood to oxygen, wherein the exposing to oxygen step occurs before the separation step or after the recombining step.

4. The method of claim 1, wherein the separating is through one or more of a filter, a centrifuge, or dialysis.

5. The method of claim 1, wherein the plasma is exposed to a concentration of nitric oxide over a period of time sufficient to reduce pathogen concentration in the blood.

6. The method of claim 1, wherein the pathogens are selected from viruses, bacteria, mycobateria, parasites, and fungi.

7. The method of claim 1, wherein the nitric oxide containing gas is controllably introduced in relation to an amount of plasma separated from the blood.

8. The method of claim 1, wherein the exposing step comprises:
providing a semipermeable membrane selectively permeable to nitric oxide gas and impermeable to nitrogen gas adapted to allow contact of an outside of the membrane with the plasma; and
delivering nitric oxide containing gas to an inside of the membrane under pressure sufficient to drive the nitric oxide across the membrane for contact with the plasma on the outside of the membrane within a desired concentration range sufficient to reduce pathogen concentration in the plasma.

9. The method of claim 1, wherein the concentration of nitric oxide in the nitric oxide containing gas is about 120 ppm to about 400 ppm.

10. The method of claim 9, wherein the concentration is about 160 ppm to about 220 ppm.

11. The method of claim 1, wherein the concentration of nitric oxide in the nitric oxide containing gas is less than about 120 ppm and more than 0.

12. The method of claim 1, wherein before the combining the exposed plasma with the blood cells step, the exposed plasma is treated by a bacterial particulate filter to reduce levels of lipopolysaccharide (LPS) in the plasma.

13. An extracorporeal blood circuit comprising:
an inlet line adapted to obtain blood from a mammal or a blood source;
an outlet line adapted to return blood to the mammal or blood source;
a fluid circuit for fluid communication between the inlet and the outlet line, wherein the fluid circuit comprises:
at least one pump acting on the fluid circuit to circulate the blood therethrough;
a separation unit in fluid communication with the inlet line, wherein the separation unit is adapted to separate the blood received from the mammal or source into plasma and blood cells;
a nitric oxide unit that exposes the plasma with a nitric oxide containing gas;
a mixer for combining the exposed plasma with the blood cells; and
a reduction unit for reducing the nitric oxide content in the recombined blood, wherein the reduction unit is in fluid communication with the outlet line and contacts the recombined blood with a gaseous source having a nitric oxide content that is less than the recombined blood.

14. The extracorporeal blood circuit of claim 13, further comprising one or more of a reservoir to collect the blood from the mammal or source, an oxygenator, a dialysis component, an organ perfusion component, a heat exchange component, and an oxygenation component.

15. The extracorporeal blood circuit of claim 13, wherein the gaseous source is ambient air.

16. The extracorporeal blood circuit of claim 13, wherein the separation unit comprises one or more of a filter, a centrifuge, and dialysis.

17. The extracorporeal blood circuit of claim 13, wherein the nitric oxide unit comprises:
a semipermeable membrane selectively permeable to nitric oxide gas and impermeable to nitrogen gas adapted to allow contact of an outside of the membrane with the plasma; and
nitric oxide containing gas deliverable to an inside of the membrane under pressure sufficient to drive the nitric oxide across the membrane for contact with the plasma on the outside of the membrane within a desired concentration range sufficient to reduce pathogen concentration in the plasma.

18. The extracorporeal blood circuit of claim 13, wherein the concentration of nitric oxide in the nitric oxide containing gas is about 120 ppm to about 400 ppm.

19. The extracorporeal blood circuit of claim 18, wherein the concentration is about 160 ppm to about 220 ppm.

20. The extracorporeal blood circuit of claim 13, wherein the concentration of nitric oxide in the nitric oxide containing gas is less than about 120 ppm and more than 0.

21. The extracorporeal blood circuit of claim 13, further comprising a bacterial particulate filter to reduce levels of lipopolysaccharide (LPS) in the plasma.

22. A method of reducing pathogens in blood, the method comprising:
obtaining blood from a mammal or a blood source;
separating the blood into plasma and blood cells;
exposing the plasma to nitric oxide containing gas;
combining the exposed plasma with the blood cells;
reducing nitric oxide gas content in the recombined blood by providing a semipermeable membrane selectively permeable to nitric oxide gas in between the recombined blood and a gaseous source; and
returning the recombined blood to the mammal or blood source.

23. The method of claim 22, wherein the gaseous source is ambient air.

24. The method of claim 22, further comprising exposing the blood to oxygen, wherein the exposing to oxygen step occurs before the separation step or after the recombining step.

25. The method of claim 22, wherein the separating is through one or more of a filter, a centrifuge, or dialysis.

26. The method of claim 22, wherein the plasma is exposed to a concentration of nitric oxide over a period of time sufficient to reduce pathogen concentration in the blood.

27. The method of claim 22, wherein the pathogens are selected from viruses, bacteria, mycobateria, parasites, and fungi.

28. The method of claim 22, wherein the nitric oxide containing gas is controllably introduced in relation to an amount of plasma separated from the blood.

29. The method of claim 22, wherein the exposing step comprises:
providing a semipermeable membrane selectively permeable to nitric oxide gas and impermeable to nitrogen gas adapted to allow contact of an outside of the membrane with the plasma; and
delivering nitric oxide containing gas to an inside of the membrane under pressure sufficient to drive the nitric oxide across the membrane for contact with the plasma on the outside of the membrane within a desired concentration range sufficient to reduce pathogen concentration in the plasma.

30. The method of claim 22, wherein the concentration of nitric oxide in the nitric oxide containing gas is about 120 ppm to about 400 ppm.

31. The method of claim 30, wherein the concentration is about 160 ppm to about 220 ppm.

32. The method of claim 22, wherein the concentration of nitric oxide in the nitric oxide containing gas is less than about 120 ppm and more than 0.

33. The method of claim 22, wherein before the combining the exposed plasma with the blood cells step, the exposed plasma is treated by a bacterial particulate filter to reduce levels of lipopolysaccharide (LPS) in the plasma.

34. An extracorporeal blood circuit comprising:
an inlet line adapted to obtain blood from a mammal or a blood source;
an outlet line adapted to return blood to the mammal or blood source;
a fluid circuit for fluid communication between the inlet and the outlet line, wherein the fluid circuit comprises:
at least one pump acting on the fluid circuit to circulate the blood therethrough;
a separation unit in fluid communication with the inlet line, wherein the separation unit is adapted to separate the blood received from the mammal or source into plasma and blood cells;
a nitric oxide unit that exposes the plasma with a nitric oxide gas containing gas;
a mixer for combining the exposed plasma with the blood cells; and
a reduction unit for reducing the nitric oxide content in the recombined blood, wherein the reduction unit is in fluid communication with the outlet line and comprises a semipermeable membrane selectively permeable to nitric oxide gas operably fitted in between the combined blood and a gaseous source.

35. The extracorporeal blood circuit of claim 34, further comprising one or more of a reservoir to collect the blood from the mammal or source, an oxygenator, a dialysis component, an organ perfusion component, a heat exchange component, and an oxygenation component.

36. The extracorporeal blood circuit of claim 34, wherein the gaseous source is ambient air.

37. The extracorporeal blood circuit of claim 34, wherein the separation unit comprises one or more of a filter, a centrifuge, and dialysis.

38. The extracorporeal blood circuit of claim 34, wherein the nitric oxide unit comprises:
a semipermeable membrane selectively permeable to nitric oxide gas and impermeable to nitrogen gas adapted to allow contact of an outside of the membrane with the plasma; and
nitric oxide containing gas deliverable to an inside of the membrane under pressure sufficient to drive the nitric oxide across the membrane for contact with the plasma on the outside of the membrane within a desired concentration range sufficient to reduce pathogen concentration in the plasma.

39. The extracorporeal blood circuit of claim 34, wherein the concentration of nitric oxide in the nitric oxide containing gas is about 120 ppm to about 400 ppm.

40. The extracorporeal blood circuit of claim 39, wherein the concentration is about 160 ppm to about 220 ppm.

41. The extracorporeal blood circuit of claim 34, wherein the concentration of nitric oxide in the nitric oxide containing gas is less than about 120 ppm and more than 0.

42. The extracorporeal blood circuit of claim 34, further comprising a bacterial particulate filter to reduce levels of lipopolysaccharide (LPS) in the plasma.

* * * * *